(12) United States Patent
Eidenschink et al.

(10) Patent No.: US 6,970,734 B2
(45) Date of Patent: Nov. 29, 2005

(54) FLEXIBLE MARKER BANDS

(75) Inventors: Tracee E. J. Eidenschink, Wayzata, MN (US); Scott E. Arndt, St. Michael, MN (US); Brian J. Brown, Hanover, MN (US); Melissa Ann Frenkel, Minneapolis, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/308,251

(22) Filed: Dec. 2, 2002

(65) Prior Publication Data

US 2004/0106913 A1 Jun. 3, 2004

(51) Int. Cl.⁷ ............................................. A61B 5/05
(52) U.S. Cl. .................. 600/424; 604/529; 604/103.1
(58) Field of Search ................. 604/523, 529, 604/96.01, 103.1; 600/433–435, 424, 485; 606/191, 194, 192

(56) References Cited

U.S. PATENT DOCUMENTS

| | | | |
|---|---|---|---|
| 4,105,732 A | 8/1978 | Slingluff .................... 264/104 |
| 4,733,665 A | 3/1988 | Palmaz ....................... 606/108 |
| 4,740,207 A | 4/1988 | Kreamer ........................ 623/1 |
| 4,866,132 A | 9/1989 | Obligin et al. .............. 525/107 |
| 5,007,926 A | 4/1991 | Derbyshire ..................... 623/1 |
| 5,024,232 A | 6/1991 | Smid et al. ................. 128/654 |
| 5,256,334 A | 10/1993 | Smid et al. ................. 252/478 |
| 5,318,535 A | 6/1994 | Miraki ........................ 604/102 |
| 5,372,138 A * | 12/1994 | Crowley et al. ............ 600/463 |
| 5,429,597 A | 7/1995 | DeMello et al. .............. 604/49 |
| 5,531,715 A * | 7/1996 | Engelson et al. ........... 604/265 |
| 5,551,444 A | 9/1996 | Finlayson .................... 128/772 |
| 5,702,682 A | 12/1997 | Thompson ................. 424/9.42 |
| 5,728,079 A | 3/1998 | Weber et al. ............... 604/280 |
| 5,759,174 A | 6/1998 | Fischell et al. ............... 604/96 |
| 5,779,731 A | 7/1998 | Leavitt ........................ 606/194 |
| 5,807,279 A | 9/1998 | Viera ......................... 600/585 |
| 5,846,199 A * | 12/1998 | Hijlkema et al. ........... 600/435 |
| 5,858,556 A | 1/1999 | Eckert et al. ............... 428/586 |
| 5,899,890 A * | 5/1999 | Chiang et al. .............. 604/264 |
| 5,948,489 A | 9/1999 | Hopkins .................... 428/34.9 |
| 6,036,682 A | 3/2000 | Lange et al. ................ 604/529 |
| 6,210,396 B1 | 4/2001 | MacDonald et al. ........ 604/529 |
| 6,285,903 B1 * | 9/2001 | Rosenthal et al. .......... 600/433 |
| 6,520,934 B1 * | 2/2003 | Lee et al. ................. 604/103.1 |
| 6,540,721 B1 * | 4/2003 | Voyles et al. ............. 604/103.1 |
| 6,648,879 B2 * | 11/2003 | Joye et al. ..................... 606/21 |
| 2003/0167052 A1 | 9/2003 | Lee et al. .................... 604/259 |
| 2004/0019280 A1 * | 1/2004 | Waner et al. ............... 600/466 |
| 2004/0086674 A1 * | 5/2004 | Holman ...................... 428/36.9 |
| 2004/0116901 A1 * | 6/2004 | Appling ...................... 604/523 |

FOREIGN PATENT DOCUMENTS

WO 99/48548 9/1999

* cited by examiner

*Primary Examiner*—Cris L. Rodriguez
(74) *Attorney, Agent, or Firm*—Vidas, Arrett, Steinkraus

(57) ABSTRACT

A catheter assembly comprises a catheter shaft having a first region and a second region. The first region is less radiopaque than the second region. The first region is constructed of a shaft material and the second region is constructed from the shaft material in combination with at least one radiopaque material. At least a portion of the shaft material of the second region defines at least one grooved region. The at least one radiopaque material is positioned at least partially within the at least one grooved region.

11 Claims, 2 Drawing Sheets

FLEXIBLE MARKER BANDS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Medical devices such as stents, stent-grafts, grafts, or vena cava filters and catheters, balloon catheters, and medical balloons for their delivery are utilized in a number of medical procedures and situations, and as such their structure and function are well known.

Catheters for example, may be used in a variety of medical procedures. An example of one potential use for a catheter is in PTCA procedures. In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, to radially compress the arthrosclerotic plaque of the lesion against the inside of the artery wall and thereby dilate the lumen of the artery. The balloon is then deflated to a small profile so that the dilatation catheter may be withdrawn from the patient's vasculature and blood flow resumed through the dilated artery.

In angioplasty procedures of the kind described above, there may be injury to or restenosis of the artery, which either necessitates another angioplasty procedure, a surgical by-pass operation, or some method of repairing or strengthening the area. To strengthen the area and help prevent restenosis, a physician can implant an intravascular prosthesis for maintaining vascular patency, commonly called a stent, inside the artery at the lesion. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. Nos. 4,740,207 and 5,007,926 among others. Several patent references such as U.S. Pat. No. 4,733,665 describe introduction of a stent over a balloon catheter.

To assist in accurate placement of the catheter and stent underneath the lesion site it is useful to visually monitor the catheter as it advances through a vessel. Fluoroscopes, X-ray machines or other similar viewing devices are used to view the catheter within the body as it is advanced. However, in order for the catheter to be visible the catheter, or a portion of the catheter, must be radiopaque. In previous catheter designs radiopaque: marker bands, stent retaining members, hubs, catheter tips, or other components have been attached to the catheter for this purpose.

An example of a catheter which utilizes an external metal radiopaque marker band is U.S. Pat. No. 5,759,174 to Fischell et al., which has a single external metal marker band which is intended to identify the central portion of a stenosis once the delivery catheter is removed. Marker bands such as those disclosed by Fischell et al. are mounted externally on the balloon of an angioplasty catheter and undesirably increase the profile of the catheter as well as its cost. Furthermore, such marker bands are constructed from expensive and heavy radiopaque metals such as gold, platinum and tantalum or alloys of these dense materials. The use of these heavy materials typically results in marker bands that are somewhat inflexible which may impair the trackability of the delivery catheter.

Despite these shortcomings, often times marker bands are preferable over radiopaque tips alone, since a radiopaque catheter tip only provides for the end of the catheter to be visible as opposed to a desired area along the catheter shaft. For example, U.S. Pat. No. 5,429,597 to Demello et al., discloses a balloon catheter having a radiopaque distal tip composed of a polymer mixed with a radiopaque powder such as tungsten.

Other references are known which provide for various radiopaque polymer complexes. For example: U.S. Pat. Nos. 4,866,132; 5,256,334; and 5,024,232, respectively disclose various methods of making radiopaque polymer complexes. In addition, the use of a compliant material to form a marker band which surrounds the external surface of a catheter body is described in U.S. Pat. No. 5,948,489.

In addition to utilizing radiopaque marker bands for observing the catheter as it is advanced through a body lumen, radiopaque materials may also be utilized in the formation of other potential catheter components such as hubs, bumpers, stops and others.

In many applications where a catheter is used to delivery a stent, graft, stent-graft, vena-cave filter, and other implantable medical devices, collectively referred to herein as stents, the inner shaft or member of the catheter, which supports the stent prior to delivery, will often employ one or more radiopaque marker bands that are positioned adjacent to one or more of the ends of the stent. The marker bands are often crimped or otherwise affixed to the inner shaft so as not to underlie the stent. Where the catheter employs a balloon for expanding or seating the stent, the stent is disposed about the body of the balloon, whereas the marker bands are positioned on the inner shaft to underlie the cones of the balloon and fall outside the balloon body and stent. The marker bands are positioned outside the length of the stent to prevent the balloon from being potentially damaged by the marker bands.

However, because the marker bands do not underlie the stent, the ability to position the stent accurately may be compromised. Furthermore, because the marker bands do not underlie the body of the balloon the precise deployment area of the balloon and thus the precise deployment area of the stent may be difficult to determine.

In light of the above, it would be desirable to provide for a catheter shaft or portion thereof that includes a radiopaque area corresponding to the length of the balloon body and/or the length of the stent to be retained thereon. The radiopaque area of the catheter shaft is constructed and arranged to allow the stent to be crimped directly thereto. Where the catheter employs a balloon, a stent may be crimped directly to the portion of the balloon that overlies the radiopaque area of the catheter shaft.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. For example, at least one embodiment of the invention is directed to a flexible radiopaque marker band that may be a portion of a catheter shaft, and/or be incorporated onto a portion of the catheter shaft.

In at least one embodiment of the invention the radiopaque marker band defines a length of the catheter shaft that defines or underlies a stent mounting region.

In at least one embodiment of the invention the radiopaque marker band defines a length of the catheter shaft that underlies at least the body portion of a balloon.

In at least one embodiment the catheter shaft defines an area having one or more surface features, such as one or more grooves, valleys, indentations, pores, etc. The radiopaque material overlays or is inserted into the one or more surface features.

In some embodiments at least one region of the catheter shaft includes radiopaque material that is positioned on or within the material of the shaft according to a predetermined pattern.

In at least one embodiment one or more radiopaque members or wires are engaged to at least a portion the catheter shaft. In some embodiments the wire is force fit onto the exterior of the catheter shaft or into the material of the catheter shaft.

In at least one embodiment a flexible sheath comprises on or more radiopaque materials, the sheath may be disposed about a portion of the catheter shaft and/or may be fitted into a recess defined by the catheter shaft.

In at least one embodiment the radiopaque material is a radiopaque metal, radiopaque polymer, and any combination thereof.

In at least one embodiment the radiopaque material is MRI compatible.

Some embodiments of the invention are directed to one or more methods of forming a radiopaque catheter shaft, to which a balloon and/or stent may be disposed or positioned thereabout.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
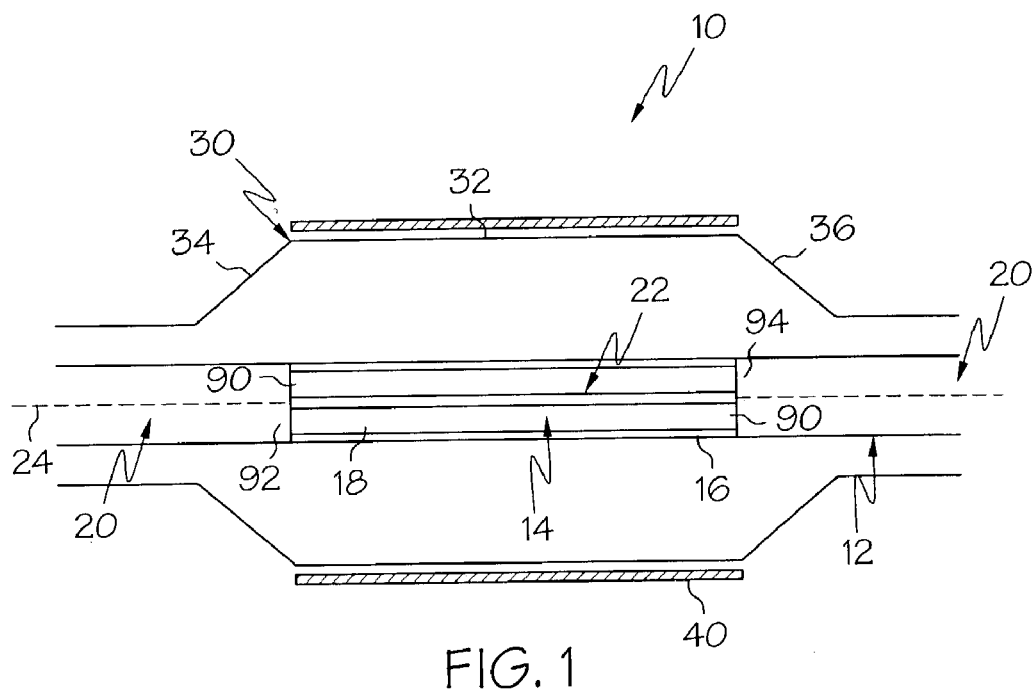
FIG. 1 is a side view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, the present invention may be embodied in a variety of forms. In FIG. 1 an embodiment of the invention is shown comprising a catheter, indicated generally at 10. Catheter 10 includes an inner shaft 12 which defines at least one radiopaque region 14. Region 14 of the shaft 12 is constructed of at least two different materials, namely at least one radiopaque material 16 and the shaft material 18. The radiopaque material 16 is arranged according to a predetermined pattern on or at least partially within the shaft material 18.

A region or regions 20 of the shaft 12 adjacent to the radiopaque region 14 do not include the radiopaque material 16 in their construction. However, adjacent regions 20 may be somewhat radiopaque depending on the radiopaque qualities of the shaft material 18. By combining radiopaque material 16 with the shaft material 18, the region 14 is made more radiopaque than any adjacent region 20 of the shaft 12.

Shalt material 18 is typically an extruded polymeric material. Some examples of shaft material 18 include, but are not limited to: high density polyethylene (HDPE), polytetrafluoroethylene (PTFE), Nylon, block copolymers of polyamide and polyether such as PEBAX available from made by Elf Atochem, polyether-ester copolymer such as HYTREL available from Dupont Co., etc. Shaft material maybe selected from HDPE, PTFE, Nylon, block copolymers of polyamide and polyether, polyether-ester copolymer, and any combinations thereof.

Radiopaque material 16 may be one or more radiopaque metals including but not limited to: gold, tungsten, iridium, rhodium, platinum, barium, bismuth and combinations and/or alloys thereof. The material 16 may be exposed or 'bare', or be at least partially embedded in a polymer material, such as that of the shaft material. To provide for a radiopaque material more suitable for use in MRI applications, the material 16 may be nanocrystallized particles made of transition metal oxides. For example: $CoFeO_4$, $MnFe_2O_4$, $MgFe2O4$, etc. could be utilized as, or in conjunction with other materials to provide radiopaque material 16.

In some embodiments the radiopaque material 16 is a radiopaque polymer. Such a polymeric material may comprise a matrix of a polymer material in combination with a radiopaque metal, such as are described above. Other radiopaque polymers as are known may also be used in providing for radiopaque material 16.

As is shown in FIG. 1, the radiopaque material 16 is arranged as one or more stripes or members 22. The members 22 may be arranged in any manner desired within region 14 of the shaft 12. In at least one embodiment the members 22 are oriented to be substantially parallel to a longitudinal axis 24 of the shaft 12. Other configurations may also be provided for.

Because region 14 is at least partially defined by the presence of radiopaque material 16, a member or members 22 have a longitudinal length that is substantially equal to that of the region 14.

In some embodiments the catheter 10 includes a balloon or other inflatable device 30 that is disposed about the shaft 12. The balloon comprises a balloon body 32 which is between balloon cones 34 and 36. The balloon 30 is positioned about the shaft 12 so that the balloon body 32 overlies the region 14. As a result the length of the balloon body is at least as long as the length of the region 14.

In some embodiments the length of the body 32 is substantially equal to the length of the region 14.

Where the catheter 10 is used for delivery of a medical device such as a stent, graft, stent-graft, vena-cava filter, or other implantable medical device, hereinafter collectively referred to as a stent or stents, a stent 40 is disposed about the shaft 12. In some embodiments the stent 40 is positioned about the shaft 12 in such a manner as to ensure that the stent 40 overlies the radiopaque region 14 so that the stent 40 does not extend substantially beyond the length of the radiopaque region 14 and the radiopaque region 14 does not extend substantially beyond the length of the stent 40.

Where the catheter 10 employs a balloon 30 to deliver the stent 40 the stent 40 is engaged to the balloon body 32. Thus, the stent 40 and balloon body 32 have substantially the same length as the radiopaque region 14 and share a substantially equivalent longitudinal position relative to the shaft 12.

Where the radiopaque material 16 is arranged as one or more members 22, the members may be arranged about and/or within the region 14 in a variety of different ways. For example in the embodiment shown in FIG. 2, the radiopaque material 16 comprises a plurality of members 22 that extend longitudinally with the region 14. The members 22 may be wires of radiopaque metal such as previously described. Alternatively, the members 22 may be extruded or molded members, braided or otherwise, of one or more radiopaque polymers.

Figure 2:
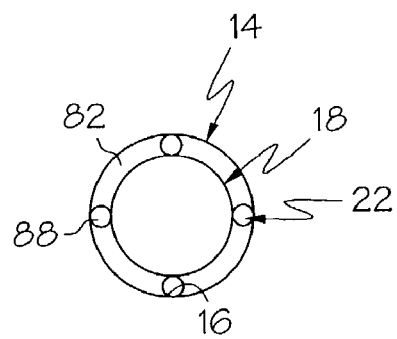
FIG. 2 is a cross-sectional view of an embodiment of the invention.

In the embodiment shown in FIG. 2, the members 22 are at least partially enclosed within the shaft material 18 of the region 14. In at least one embodiment the members are completely enclosed by the shaft material 18, however in some embodiments, an exposed edge or surface of the member 22 may be exposed through the outer surface of the shaft material 18. The members 22 may be placed within and/or about the shaft material 18 in accordance with a variety of different methods.

In many cases shaft material 18 is softer than the radiopaque material 16, particularly where the radiopaque material is a metal wire or other member 22. In such a case the members 22 may be directly imbedded into the shaft material 18 by directly applying a force to the members 22 which is sufficient to push the members 22 at least partially within the shaft material 18 of the region 14.

Figure 3:
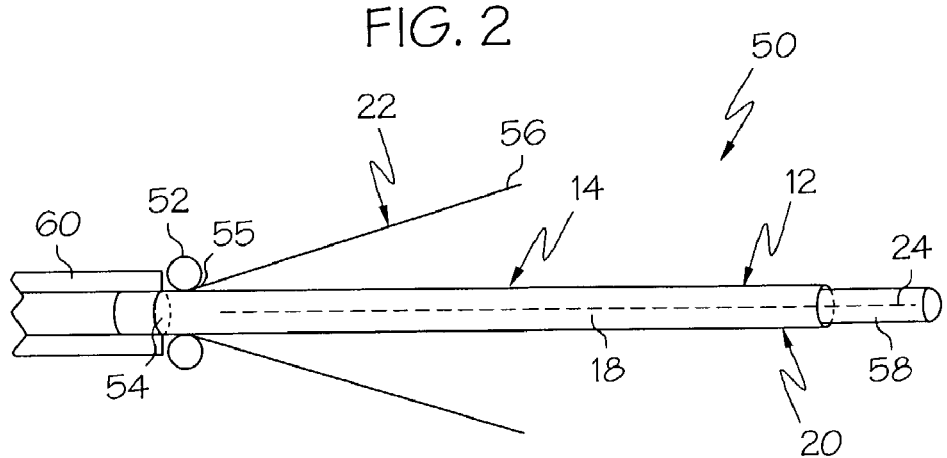
FIG. 3 is a side view of an embodiment of the invention illustrating a method of forming a radiopaque portion of a catheter shaft.

In at least one embodiment a roller assembly, indicated generally at 50, in FIG. 3 includes a plurality of force applicators such as rollers 52 which are arranged to define an opening 54 through which the catheter shaft 12, or portion there of such as region 14, is threaded therethrough. The opening 52 has a diameter substantially equal or less than the diameter of a region 20 of the shaft 12. In order to imbed one or more members 22 into the shaft material 18, a first end 55 of each member 22 is engaged to the shaft material 18, where the shaft 12 is to be inserted into the opening 54. The second end 56 of each member is held in tension at an angle off set from the longitudinal axis 24 of the shaft 12. As the shaft 12 is threaded through the opening 54, the rollers press the members 22 into the shaft material 18. The length of the members 22 pressed into the shaft material 18 defines the length of the radiopaque region 14.

In order to prevent the shaft 12 from being substantially deformed by the rollers 52, the shaft 12 is disposed about an inner mandrel or other support member 58. In some embodiments an outer mandrel 60 assists in keeping the outer diameter of the entire shaft 12 substantially constant.

In some embodiments one or more of the rollers 52 and/or members 22 may be heated to aid in deforming the shaft material 18 to an extent sufficient to allow the members 22 to be partially or fully embedded therein.

Figure 4:
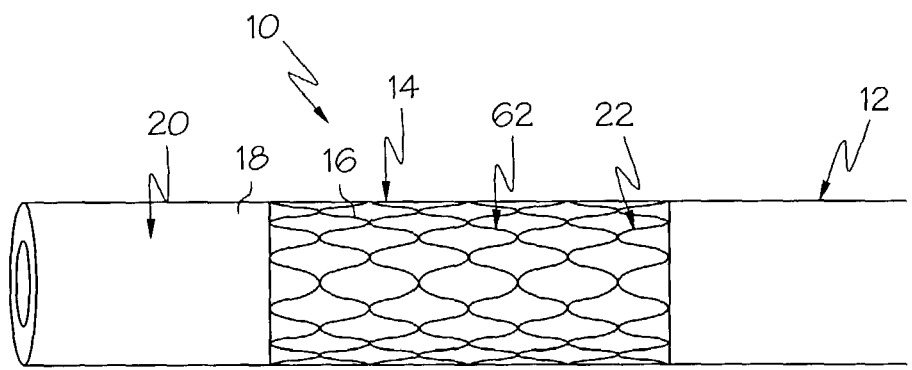
FIG. 4 is a perspective view of an embodiment of the invention.

In some embodiments the members 22 may be configured into a pattern 62 of interconnected members such as is shown in FIG. 4. The pattern 62 may have any configuration, shape, or design. In one embodiment the shaft 12 shown in FIG. 4 is formed by placing the pattern 62 of radiopaque material 16 over the shaft 12 and then passing the shaft 12 through the roller assembly as previously described. The resulting shaft 12 comprises a radiopaque region 14 corresponding to the longitudinal length of the pattern 62.

Figure 5:
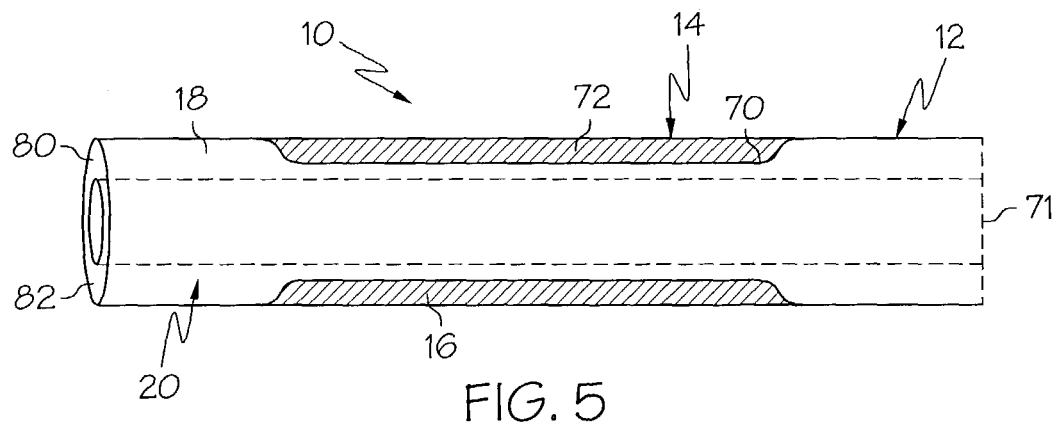
FIG. 5 is a perspective view of an embodiment of the invention.
Figure 6:
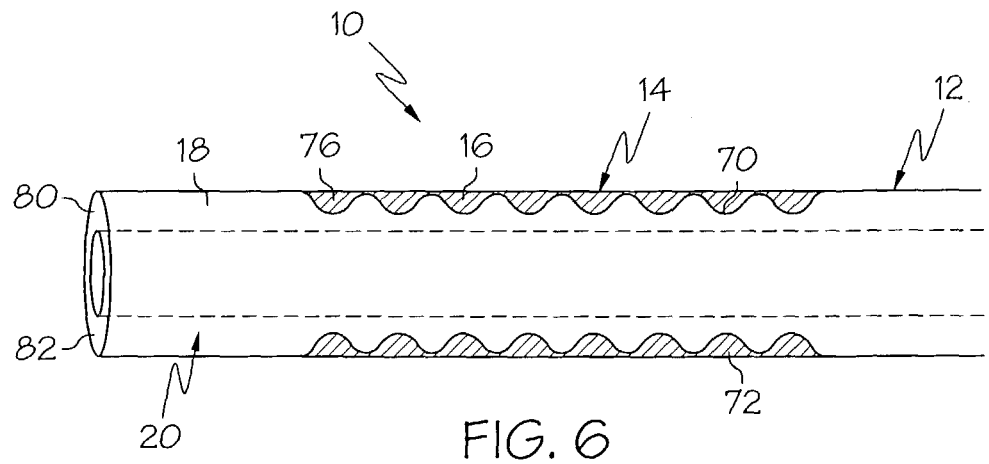
FIG. 6 is a perspective view of an embodiment of the invention.

In some embodiments, such as is shown in FIGS. 5 and 6, the radiopaque region 14 is formed by providing the shaft 12 with one or more indentations, grooves, pores or other surface features 70 which are suitable for the receipt of a radiopaque material 16. Following insertion or application of the radiopaque material 16 to the selected surface feature 70, the shaft 12 is seen to have an outer diameter 71 that is substantially the same in the region 14 as well as in adjacent region(s) 20.

In FIG. 5 the shaft 12 employs a single radial indentation or groove 70 that extends longitudinally to define the length of the region 14. A sheath or sleeve 72 of radiopaque material 16 is positioned about the shaft material 18 of the region 14. The sheath is sufficiently thick to provide the region 14 with an outer diameter that is substantially the same as the outer diameter of the adjacent regions 20 as defined by the shaft material 18 alone.

In some embodiments it may be desirable however, to provide for a region 14, or portion(s) thereof, of radiopaque material 16 that has a diameter greater than the diameter of one or more of the adjacent regions 20. For example, where a stent 40 such as is shown in FIG. 1 is disposed about the region 14, the radiopaque material 16 may comprise one or more protrusions, hubs or other surface features suitable for engaging the stent in the unexpanded state.

In FIG. 6 the shaft employs a plurality of radial indentations or valleys 70 that may be filled with on or more bands 76 of radiopaque material 16 or a sheath 72 having a contoured shape to match the pattern and depth of the valleys. The bands may be comprised of one or more radiopaque metals and/or radiopaque polymers.

Indentations 70 such as are shown in FIGS. 5 and 6, may be formed by varying the extrusion rate of the shaft material 18, ablating, cutting or otherwise removing selected portions of the shaft material 18 to a desired depth, or by simply by applying sufficient force to a supported catheter shaft 12 to cause the outer diameter in the region 14 to be deformed.

The depth of the indentations 70 may be varied but the depth does not extend through the thickness of the shaft wall. For example, in the embodiments shown in FIGS. 5 and 6 the shaft wall 80 has a thickness 82 of about 0.002 to about 0.008 inches. The depth of the indentation or indentations 70 is about 0.001 to about 0.004 inches of the wall thickness 82. Thus, radiopaque material 16 may have a depth of about 0.001 to about 0.004 inches in order to ensure that the outer diameter of the region 14 is substantially the same as the outer diameter of the adjacent region(s) 20. In some embodiments the depth of the radiopaque material 16 is about 0.002 to about 0.003 inches.

In some embodiments, where a member 22 of radiopaque material 16 is positioned substantially within the shaft material 18 of the region 14, such as shown in FIG. 2 the member 22 will have a diameter 88 that is less than the wall thickness 82. In at least one embodiment the diameter 88 of the members 22 is about 0.001 to about 0.0015 inches.

In the embodiment shown in FIG. 4, the shaft 12 may be constructed according to methods other than those listed above. For example, a laser or other cutting/ablation device may be used to cut a pattern of grooves or indentations into the shaft material 18, the pattern 62 of radiopaque material 16 may then be placed within the indentations to from the radiopaque region 14.

Numerous other methods may all so be used for constructing the various embodiments shown in FIGS. 1–2, and 4–6. According to at least one method a length of shaft material 18 is provided with radiopaque material 16 to form the region 14. The region 14 is joined to separate regions 20 of shaft material 18 to from the completed shaft 12. As is shown in FIG. 1, the ends 90 of the radiopaque region 14 may be bonded or welded, such as by butt-welding, to the respective ends 92 and 94 of the respective adjacent regions 20.

In some embodiments, the radiopaque material 16 has a greater degree of rigidity or stiffness than the shaft material 18. As a result, the radiopaque region 14 may be provided with greater longitudinal stiffness which may provide the catheter 10 with improved push characteristics.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A catheter assembly comprising:
    a catheter shaft, the catheter shaft comprising a first region and a second region, the first region being less radiopaque than the second region, the first region being constructed of a material, at least a portion of the second region being defined by a grooved pattern of the material in combination with at least one radiopaque material, the at least one radiopaque material comprises at least one radiopaque metal, the at least one radiopaque metal is at least one wire, the grooved pattern comprising a plurality of interconnected grooves, wherein at least some of the grooves have a wave-like pattern extending about the circumference of the second region.

2. The catheter assembly of claim 1 wherein the first region comprises an outer diameter and the second region comprises an outer diameter, the outer diameter of the first region being substantially equal to the outer diameter of the second region.

3. The catheter assembly of claim 1 wherein the material is a polymeric material.

4. The catheter assembly of claim 1 wherein the material is selected from at least one member of the group consisting of: HDPE, PTFE, Nylon, block copolymers of polyamide and polyether, polyether-ester copolymer, and any combinations thereof.

5. The catheter assembly of claim 1 wherein the at least one radiopaque metal is selected from at least one member of the group consisting of: gold, tungsten, iridium, rhodium, platinum, barium, bismuth, $CoFeO_4$, $MnFe2O4$, $MgFe_2O_4$, and any combinations thereof.

6. The catheter assembly of claim 1 wherein the at least one wire comprises a plurality of wires.

7. The catheter assembly of claim 1 wherein the second region defines a wall thickness, the wall thickness being about 0.002 to about 0.008 inches.

8. The catheter assembly of claim 7 wherein the at least one radiopaque material defines about 0.001 to about 0.004 inches of the wall thickness.

9. The catheter of claim 1 wherein the at least one radiopaque material is at least one polymer in combination with at least one member of the group consisting of gold, tungsten, iridium, rhodium, platinum, barium, bismuth, $CoFeO_4$, $MnFe2O4$, $MgFe_2O_4$, and any combinations thereof.

10. The catheter of claim 1 wherein the at least one grooved region has a depth of about 0.001 to about 0.004 inches.

11. The catheter of claim 1 wherein the grooved pattern corresponds to the pattern of interconnected members.

* * * * *